United States Patent [19]
Bainville et al.

[11] Patent Number: 5,564,437
[45] Date of Patent: Oct. 15, 1996

[54] METHOD AND SYSTEM FOR DETERMINING THE FIXATION POINT ON THE FEMUR OF A CROSSED LIGAMENT OF THE KNEE

[75] Inventors: Eric Bainville; Philippe Cinquin, both of Grenoble; Remi Julliard, Herbeys; Jocelyne Troccaz, Eybens; Stephane Lavallee, Grenoble; Guillaume Champlebaux, Voiron, all of France

[73] Assignee: Universite Joseph Fourier, Grenoble, France

[21] Appl. No.: 166,032

[22] Filed: Dec. 14, 1993

[30] Foreign Application Priority Data

Dec. 15, 1992 [FR] France .................. 92 15549

[51] Int. Cl.$^6$ .................................. A61B 5/103
[52] U.S. Cl. .................. 128/774; 128/897; 128/898; 606/96; 623/13; 623/39
[58] Field of Search .................. 623/13, 16, 20, 623/39; 606/96, 97; 177/774, 782; 128/897, 898, 899

[56] References Cited

U.S. PATENT DOCUMENTS

| | | | |
|---|---|---|---|
| 4,712,542 | 12/1987 | Daniel et al. | 623/13 |
| 4,803,976 | 2/1989 | Frigg et al. | 606/97 |
| 4,964,862 | 10/1990 | Arms | 623/13 |
| 5,037,426 | 8/1991 | Goble et al. | 623/13 |
| 5,230,623 | 7/1993 | Guthrie et al. | 178/774 |

FOREIGN PATENT DOCUMENTS 9005819 7/1990 Germany.

OTHER PUBLICATIONS

"Operation Aid for Head & Neck Surgeons", Innovation et Technologie en Biologie et Medicine, vol. 13, No. 4, pp. 410–424, 1992.

"Igor: Image Guided Optical Robot", Innovation et Technologie en Biologie et Medecine, vol. 13, No. 4, pp. 375–393, 1992.

*Primary Examiner*—Lee S. Cohen
*Attorney, Agent, or Firm*—Lowe, Price, LeBlanc & Becker

[57] ABSTRACT

A method for determining the position of a point F1 of a femur with respect to a point T1 of a tibia such that the distance between F1 and T1 is substantially invariant. The method uses a three-dimensional locating system including triplets of emitting elements especially including a pointer that can be located by the system, and includes the steps of linking a first triplet to the first organ; pointing with the pointer at the position of point T1 and locating this position with respect to the position of the first triplet; pointing with the pointer at the positions of an assembly of second points that are positioned within an area of the femur where the invariant point is likely to be found; calculating the distances separating point from each of points Fi; moving the tibia with respect to the femur add calculating the variations in the distances; and selecting point F1 for which the distance is invariant.

9 Claims, 1 Drawing Sheet

METHOD AND SYSTEM FOR DETERMINING THE FIXATION POINT ON THE FEMUR OF A CROSSED LIGAMENT OF THE KNEE

BACKGROUND OF THE INVENTION

1. Field of the Invention

The present invention relates to the localization of positions of complex-shaped organs exerting complex movements one with respect to the other.

More particularly, the present invention aims, for such organs, at locating points of an organ exerting specific movements with respect to another organ, for example, points of an organ whose distance remains invariant during the movement of this organ with respect to another organ.

The invention can be used in complex mechanical systems in which it is practically impossible to determine by calculation the movement of some organs with respect to other organs. More particularly, the invention applies in case of physiologic organs and will be described hereinafter in the surgical field, and more particularly the orthopaedic surgery of the knee.

2. Discussion of the Related Art

There are clinical situations in which it is necessary to link two organs, while taking into account certain medical constraints. This particularly applies for surgery of the knee, and more precisely during repair of one or more crossed ligaments injured by a trauma.

This surgical operation consists in replacing one or several ligaments by an implant taken from the patient (generally from his kneecap tendon) or by an artificial ligament. To be efficient, this implant must be at the limit of stress during all normal movements (flexion-extension-rotation) of the knee. If the ligament is too tightened, it will rapidly break; if the ligament is too loose, it will not disallow abnormal movements. Thus, the medical constraint can be translated into an isometry constraint: the ligament must maintain a constant length during flexion-extension movements.

To achieve this purpose, the ligament must be positioned in such a way that the distance between its fixation points on the femur and tibia remains constant. To determine these points, the surgeon has a knowledge about anatomy and physiology that can be complemented by various devices. The tibial point is theoretically easy to see, both in conventional surgery and in arthroscopy because it is clearly delineated, and the surgeon knows where it is positioned with respect to the front edge of the top portion of the tibial notch. It has been demonstrated that a small variation in its position little affects the ligament's isometry. In contrast, the femoral point is positioned very deep in the trochlear throat; so, the surgeon can only roughly visually determine its position. In practice, it has been evidenced that a small variation in the position of the femoral point could substantially impair the ligament's isometry. Accordingly, to guide the selection of the femoral point, it has been suggested to position a spring and to check by flexion-extension movements whether the fixation points where this spring is fastened maintain the isometry (and therefore the isometric stress) of the spring. Once the fixation points are positioned, one must be able of sighting them. Indeed, to be strongly fixed, the ligament is introduced into femoral and tibial tunnels. The realization of the tibial tunnel does not raise any particular problem, both in conventional surgery as in arthroscopy. The femoral tunnel can be carried out in two manners: either from the outside to the inside, or from the inside to the outside (blind tunnel). In the first case (from the outside to the inside), the drill pierces the external cortical of the femur while being guided by a view finder—that is not always be easily used and not always as precise as desirable—towards the fixation point, at the intercondyle notch. The drill must be precisely positioned to arrive at the desired fixation point, any inadequate positioning having, as indicated above, detrimental consequences on the ligament's isometry. In the second case (from the inside to the outside), the drill penetrates the notch at the isometric point.

The difficulties encountered in order to precisely determine the fixation point in the femur, as well as to be absolutely sure of the precision of the drilling technique from outside to the inside of the femur tunnel, account for the difficulty of this surgical operation, both in conventional surgery and in arthroscopy. In practice, such a surgical operation:

is frequent: several thousand cases each year in France because of the importance of the functional impairment induced by the injury of the front crossed ligament; such an injury is frequent since it is caused by traumas occurring during practice of common sports (ski, football, handball, volleyball, etc.);

aims at reducing the percentage of degenerative arthrosis of knees injured by a trauma; it is admitted that, with the conventional techniques involving ligament surgery, 50% of the injured knees, that had an operation or not, will need, 25 years after the injury, a whole knee prosthesis.

The frequency and the importance of such a pathology justify the improvement of the operation technique, a key point being the improvement of the isometry of the implanted ligament.

A general object of the invention is to provide a method and a system for determining an invariant point of an organ movable with respect to another organ.

A more specific object of the present invention is to determine the position of the fixation point of a crossed ligament in the femur.

A further object of the invention is to provide a method for intervening at the previously determined fixation point.

SUMMARY OF THE INVENTION

To achieve these objects, the present invention provides a method for determining the position of a point of a second organ movable with respect to a first organ, such that the distance separating the point of the second organ from a predetermined point of the first organ is substantially invariant during the movement of the first organ with respect to the second organ. This method uses a three-dimensional system for locating triplets of emitting elements including a pointer that can be located by the system, and includes the steps consisting in linking a first triplet to the first organ; pointing with the pointer at the position of the predetermined point of the first organ and locating this position with respect to the position of the first triplet; pointing with the pointer at the positions of an assembly of second points that are located within an area of the second organ where the invariant point is likely to be found; calculating the distances separating the first point from each of the second points; moving the second organ with respect to the first organ and calculating the variations in these distances; and selecting amongst the second points the point for which the distance is substantially invariant.

The invention further includes the steps consisting in linking a second triplet to the second organ and locating the positions of the second points with respect to the second triplet.

The invention further includes the step consisting in displaying on a screen the projections of the second points on a plane.

In an application of the invention, the first organ is a tibia and the second organ is a femur, the determined point of the tibia being a first fixation point of a crossed ligament of the knee, and the invariant point of the second organ being the fixation point on the femur of this crossed ligament.

According to an embodiment of the invention, the three-dimensional locating system is a system including photodiodes and cameras.

In an application, the method according to the invention is used for the positioning of a tool at the invariant point, the tool or a guiding support of this tool is provided with a triplet of emitting elements and the tool or its support is positioned so that the operating point of the tool passes through the invariant point. The tool is for example a drill.

The present invention also provides a system implementing the above described method.

The foregoing and other objects, features, aspects and advantages of the invention will become apparent from the following detailed description of the present invention when taken in conjunction with the accompanying drawings.

DETAILED DESCRIPTION

The invention will be described more particularly with reference to the determination of the fixation point on the femur of a crossed ligament of the knee.

Figure 1:
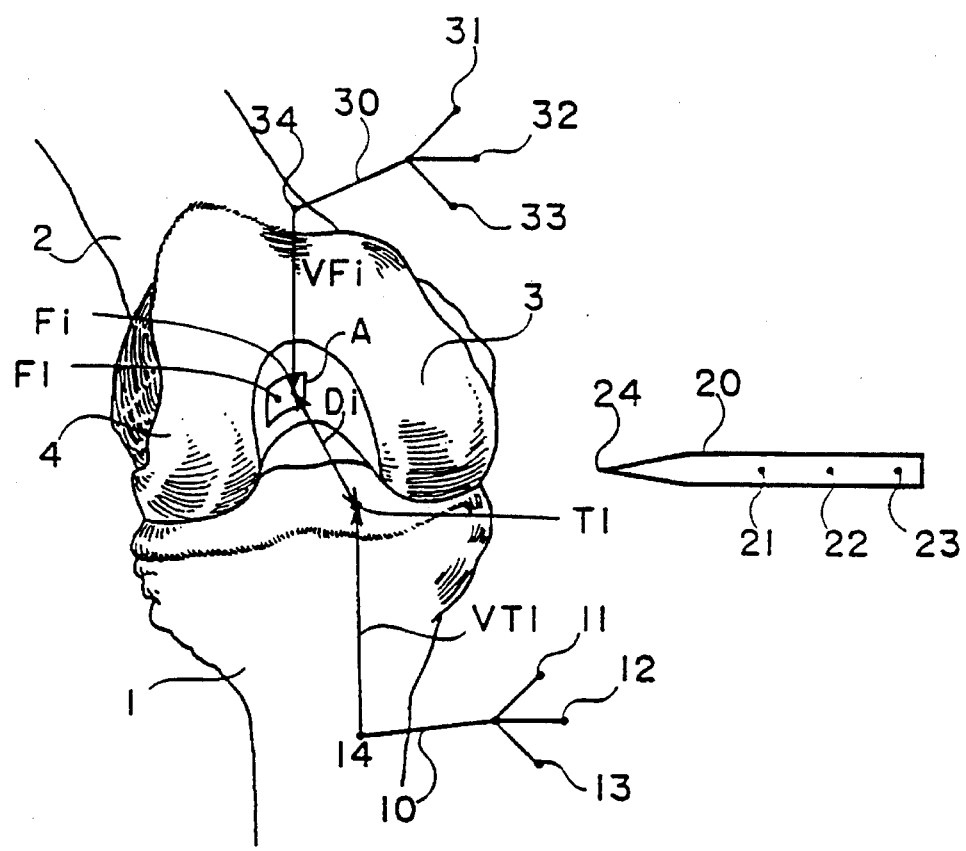
FIG. 1 schematically represents a tibia/femur articulation.

FIG. 1 schematically represents a tibia 1 and a femur 2. The femur includes two condyles 3 and 4 about which the tibia is articulated. The injured ligament to be replaced was located between a fixation point T1 on the tibia and a fixation point F1 on the femur. As indicated above, the fixation point T1 can be determined a priori by the surgeon from observation, whereas, regarding the fixation point on the femur, the surgeon only knows that it must be located within an area A that is a portion of the surface of the trochlear throat.

Known systems for locating the position of emitters, such as optical or infrared emitters use assemblies of sensors and determine the position of each emitter by triangulation. An exemplary implementation used for the determination of the head's position is described in "Innovation et Technologie en Biologie et Médecine" (ITBM) (Innovation and Technology in Biology and Medicine), volume 13, No. 4, 1992, by L. Adams et al., pp. 410–424. Systems marketed by the Northern Digital company, under the trademark "Optotrak", are also available.

One of the aspects of the invention lies in the application of such systems to the problem encountered.

Thus, the patient is placed in an environment including cameras adapted to detect the positions of photoemitters. A first set or triplet 10 of photoemitters 11, 12, 13 is fixed to the tibia at a point 14, for example, by screwing. A pointer 20 provided with photoemitters 21, 22 and 23 interacts with the detection system so as to precisely determine any position taken by its tip 24. Pointer 20 is used to point at point T1. Then, it is possible, using a conventional data processing system to determine the vector VT1 connecting point 14 to point T1 and therefore to locate point T1 for any position of the tibia.

Then, pointer 20 is used again to determine the coordinates of a series of points disposed within area A of the surface of the trochlear throat in which the desired fixation point F1 on the femur is likely to be found; then, the position of a series of pointed points F1 is memorized.

Figure 2:
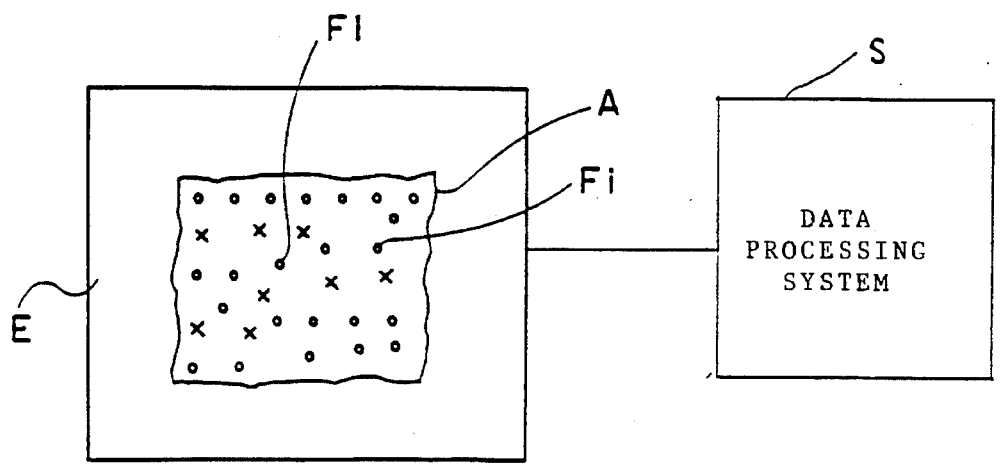
FIG. 2 represents the display on a screen of the projection of an assembly of points pointed at within a predetermined space region.

To simplify the task of the person that carries out the analysis, it is possible, using conventional means associated with the above mentioned space localization systems, and as represented in FIG. 2, to display on a screen E the localization of a planar projection of points Fi. It is also possible to determine whether the whole surface that was to be pointed at has really been analyzed. For example, if a series of points Fi, indicated by circles in FIG. 2, has been pointed at, it will be easily seen, on the screen that it would be desirable to point at additional points (represented in FIG. 2 by crosses) to carry out a regular analysis of surface A.

Using a conventional data processing systems distances Di between point T1 and each point Fi are calculated and stored. Software programs to carry out these calculations, as well as those mentioned hereinafter, can be made by any programmer who can, for example, refer to the paper by P. Cinquin et al., "IGOR: Image Guided Operating Robot", ITBM, Vol. 13, No. 4, 1992. Then, the femur being fixed in position, one makes the tibia to run its normal flexion-extension movement while detecting the resulting variations in position of triplet 10 and, correspondingly, of point T1. Simultaneously or subsequently, depending on the data processing system, the variations of each distance Di between point T1 and each point Fi are calculated, and point F1, for which the variation in distance Di was minimum during this movement, is selected amongst points Fi as the femoral fixation point.

In the above description, it has been assumed that the femur remained fixed. To avoid this constraint, according to a preferred embodiment of the invention, there is provided a second photoemitter triplet 30 including, for example, three photodiodes 31, 32, 33, that is fixed on the femur at a point 34. Triplet 30 can be located by the detection system in the same manner as triplet 10, and the vector VFi between point 34 and each point Fi can be calculated. Thus, points Fi are located even if the femur is moving.

The present invention also provides for intervening at point F1 that has been previously determined, this intervention being exactly located at point F1. For this purpose, the invention provides an intervening tool, such as a drill, also provided with photoemitters to ensure the positioning of its operating point. The photoemitters can be provided either on the tool itself, on a tool-holder guide, or on an implement visually fixing the position of the desired intervening point, such as a laser beam lighting point F1. Thus, for example, the surgeon will be able, in a first step, to position a guide in the desired way, then to drive a drill, either from point F1 towards the inside, or from the outside of the condyle towards point F1, to pierce a tunnel opening at point F1. Then, as indicated above, a natural or artificial tendon can be positioned in the tunnel thus formed.

As is apparent to those skilled in the art, various modifications can be made to the above disclosed preferred embodiments of the invention. More particularly, the invention can apply, as indicated above, to domains other than the positioning of a crossed tibia-femur tendon. Also, in the above description, there is provided a method allowing to select a point of an organ such that its distance remains invariant with respect to a point of another organ, movable with respect to the first organ. The selected point can, in other applications, be chosen as a function of any other criterion. For example, it is possible to select a point capable of a maximum movement with respect to another point, or a point moving with respect to another point, to satisfy a desired function.

We claim:

1. A method for determining the position of a point of a second organ movable with respect to a first organ, whereby the distance separating said point of the second organ from a predetermined point of the first organ is substantially invariant during the movement of the first organ with respect to the second organ and an operating point of a tool passes through the point, said method using a three-dimensional locating system including triplets of emitting elements and a pointer of said system to locate said point, wherein the method includes the following steps:

linking a first triplet to the first organ;

pointing with the pointer at the position of the predetermined point of the first organ and locating this position with respect to the position of the first triplet;

pointing with the pointer at the positions of an assembly of second points that are positioned within an area of the second organ where the invariant point is likely to be found;

calculating the distances separating the predetermined point from each of the second points;

moving the second organ with respect to the first organ and calculating the variations in said distances; and selecting amongst second points the point for which said distance is substantially invariant.

2. The method of claim 1, further including the step of linking a second triplet to the second organ and locating the positions of the second points with respect to said second triplet.

3. The method of claim 1, further including the step of displaying on a screen projections of the second points on a plane.

4. The method of claim 1, wherein the first organ is a tibia and the second organ is a femur, the predetermined point being a first fixation point of a crossed ligament of the knee, and the point of the second organ being a femoral fixation point of said crossed ligament.

5. The method of claim 1, wherein the emitting elements are photo-diodes, and said three-dimensional locating system further includes cameras adapted to detect the positions of the photo-diodes.

6. The method according to claim 1 further comprising the steps of positioning the tool or a guiding support of the tool having a triplet of emitting elements at the point so that an operating point of the tool passes through the point.

7. The method according to claim 4, wherein the tool is a drilling tool with a triplet of emitting elements, and further comprising the steps of:

providing a guiding support of the drilling tool, and drilling through the point so that an axis of the drilling passes through the point.

8. A system for determining the position of a point on a second organ movable with respect to a first organ such that the distance between said point on the second organ and a predetermined point on the first organ follows a predetermined relationship during a displacement of the first organ with respect to the second organ, said system including;

a first triplet of light emitting elements used to determine the predetermined point on the first organ;

a pointer to point at the position of the predetermined point on the first organ and at the positions of an assembly of second points that are located within an area on the second organ where a desired point is likely to be found; and means for calculating the position of the predetermined point using the first triplet, distances between the point and each of the second points, and variations of said distances when the second organ moves with respect to the first organ;

whereby it is possible to select amongst second points the point for which said distance follows said predetermined relationship.

9. The system of claim 8, further including a second triplet adapted to be associated only with the second organ and means for calculating the positions of the second points with respect to said second triplet.

* * * * *